(12) United States Patent
Renaux et al.

(10) Patent No.: US 8,480,652 B2
(45) Date of Patent: Jul. 9, 2013

(54) PERCUTANEOUS GASTROSTOMY PROBE WITH INTERNAL COLLAR AND BIODEGRADABLE END PIECE

(75) Inventors: Serge Renaux, Lamalou les Bains (FR); Pierre Senesse, Montpellier (FR)

(73) Assignee: Medwin France, Lamalou les Bains (FR)

( * ) Notice: Subject to any disclaimer, the term of this patent is extended or adjusted under 35 U.S.C. 154(b) by 571 days.

(21) Appl. No.: 12/671,343

(22) PCT Filed: Jul. 15, 2008

(86) PCT No.: PCT/FR2008/001026
§ 371 (c)(1),
(2), (4) Date: May 30, 2010

(87) PCT Pub. No.: WO2009/027600
PCT Pub. Date: Mar. 5, 2009

(65) Prior Publication Data
US 2011/0144623 A1   Jun. 16, 2011

(30) Foreign Application Priority Data
Jul. 31, 2007   (FR) ...................................... 07 05569

(51) Int. Cl.
*A61M 25/00* (2006.01)
(52) U.S. Cl.
USPC .......................................... 604/523; 604/910
(58) Field of Classification Search
USPC .................... 604/523; 605/523, 103.03, 175, 605/174, 506, 164, 910, 533, 538
See application file for complete search history.

(56) References Cited

U.S. PATENT DOCUMENTS

| 4,315,513 A |   | 2/1982 | Nawash et al. |
| 5,336,203 A | * | 8/1994 | Goldhardt et al. ............. 604/247 |

(Continued)

FOREIGN PATENT DOCUMENTS

| DE | 195 43 011 A1 | 5/1997 |
| EP | 0 238 952 A | 9/1987 |

(Continued)

OTHER PUBLICATIONS

International Search Report, Mar. 9, 2009, from International Phase of the instant application.

(Continued)

*Primary Examiner* — Kevin C Sirmons
*Assistant Examiner* — Michael J Anderson
(74) *Attorney, Agent, or Firm* — Jackson Patent Law Office

(57) ABSTRACT

A percutaneous gastrostomy catheter includes an internal retainer configured to be maintained pressed against the stomach wall and to disengage itself from a tubing by biodegradation; and an external flange, traversed by the tubing, configured to be pressed against an external face of the abdominal wall and exert, in cooperation with the internal retainer, a pressure adapted to press an external face of the stomach wall against an internal face of the abdominal wall. The internal retainer includes an internal flange. A first face of the internal flange is configured to be pressed against an internal face of the stomach wall, the internal flange being detachable from the tubing under the effect of a simple pulling force. The internal retainer also includes an end piece pressed against the second face of the internal flange, such that the internal flange is between the end piece and the external flange, the end piece being made of a completely biodegradable copolymer or polymer having a bond with the tubing.

5 Claims, 1 Drawing Sheet

U.S. PATENT DOCUMENTS

| | | | | |
|---|---|---|---|---|
| 5,391,159 A | * | 2/1995 | Hirsch et al. | 604/268 |
| 5,649,959 A | * | 7/1997 | Hannam et al. | 606/213 |
| 6,099,506 A | * | 8/2000 | Macoviak et al. | 604/173 |
| 6,186,985 B1 | * | 2/2001 | Snow | 604/175 |
| 6,673,058 B2 | * | 1/2004 | Snow | 604/506 |
| 2002/0193753 A1 | * | 12/2002 | Rouns et al. | 604/270 |
| 2002/0198440 A1 | | 12/2002 | Snow | |
| 2004/0024363 A1 | * | 2/2004 | Goldberg | 604/175 |
| 2007/0031499 A1 | * | 2/2007 | Huh et al. | 424/486 |
| 2008/0015501 A1 | * | 1/2008 | Gertner | 604/103.03 |

FOREIGN PATENT DOCUMENTS

| | | |
|---|---|---|
| WO | WO 99/17708 A | 4/1999 |
| WO | WO 2006/078672 A | 7/2006 |

OTHER PUBLICATIONS

English Translation of the Written Opinion of the International Search Authority, Mar. 31, 2010, from International Phase of the instant application.

English Translation of International Preliminary Report on Patentability Chapter I, Apr. 7, 2010, from International Phase of the instant application.

\* cited by examiner

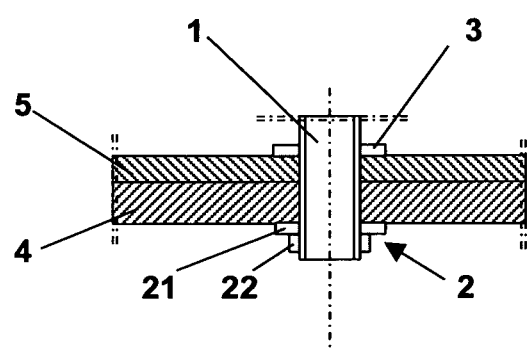

PERCUTANEOUS GASTROSTOMY PROBE WITH INTERNAL COLLAR AND BIODEGRADABLE END PIECE

FIELD OF THE INVENTION

The present invention relates to percutaneous endoscopic gastrostomy (PEG) and radiological percutaneous gastronomy (RPG) catheters enabling direct access to the gastric cavity for enteral feeding.

BACKGROUND TECHNOLOGY

Percutaneous gastrostomy is currently the standard route for prolonged enteral feeding. Due to the simplicity and speed of technology and the development of the equipment, gastroenterologists or radiologists are increasingly sought, and the placement is accessible to any endoscopist or radiologist.

There are two placement techniques:
- the endoscopic <<pull>> technique, mainly used by gastroenterologists: the steril PEG kits generally include a puncture trocar, a double strand of wire, a tubular gastrostomy catheter, a flange-type internal means of retention, an external fixation flange: are used, to grasp the intragastric wire, a diathermic cove or biopsy forceps;
- the <<push>> technique via the abdominal wall, used mainly by radiologists: in this case anchors enable binding of the stomach to the abdominal wall for the time required for the formation of adhesions between the external part of the stomach and the abdominal wall. A catheter balloon is then positioned through the abdominal wall using a dilator and a peel-off nozzle.

The catheters are generally made of silicone or polyurethane, inert and well tolerated materials. Various sizes or Charrières are available, the small catheters being blocked more easily.

There are extractable and non-extractable catheters.

Non-extractable catheters, to be replaced, should be cut flush with the cutaneous orifice. The internal device is then pushed into the stomach.

The internal means of retention can be retrieved by endoscopy, an operation that can turn out to be delicate, or evacuated via the natural routes with risks of obstruction and intestinal perforation.

The advantage of non-extractable catheters lies in their relatively rigid internal flange thus resisting an attempt of pulling out by an agitated restless patient.

The extractable catheters have a retractable removable internal flange, or a deflatable retention system, enabling their removal via the cutaneous orifice by firm tension.

The advantage of these flexible systems is to be able to pass through a severe stenosis, avoiding endoscopy, but they have less resistance to pulling out.

The choice between extractable and non-extractable catheters, made of silicone or polyurethane, depends on the indication, taking into account the advantages and disadvantages of each type of catheters.

The extractable catheters made of silicone are suitable for temporary enteral feeding.

Non-extractable or polyurethane catheters are more suitable for permanent enteral feeding or a restless patient.

The replacement of the gastrostomy catheters may be needed in case of obstruction, tube deterioration (cracking, porosity, expansion, colonization by candida).

The majority of replacement devices are catheters with a water-inflatable balloon, made of silicone. Their suitability for the gastric environment and an external retention flange enables safe use.

There is also a shorter gastrostomy button and on bare skin which, because of its aesthetic advantage and comfort, is indicated in the young or outpatient subject. It cannot be installed initially except with difficulty, however, and comes most often as replacement for a catheter already positioned in the stomach.

The catheter according to the invention is the type including:
a) a tubing designed to pass through the stomach and abdominal walls of the subject;
b) an internal means of retention, joined to the aforementioned tubing, designed to be maintained pressed against the inner face of the stomach wall and to disengage itself from the aforementioned tubing by biodegradation;
c) an external flange, traversed by the aforementioned tubing, designed to be pressed against the external face of the abdominal wall and exert, in cooperation with the internal means of retention, a pressure adapted to press the stomach wall against the abdominal wall in the area of the stoma.

The closest prior art document has the reference WO99/17708.

The internal means of retention that is described therein is constituted:
by a balloon, non-detachable from the tubing, causing, during its passage through the stoma, traumas;
by a biodegradable collar positioned between the aforementioned balloon and the stomach wall and detachable from the tubing only after total biodegradation.

SUMMARY OF THE INVENTION

The invention aims to implement a catheter of the type in question, designed to implement a new and original solution to eliminate the drawbacks mentioned above.

To that end, it relates to a percutaneous endoscopic gastrostomy catheter, which is essentially characterized in that the internal means of retention is constituted:
a) by a flange, positioned against the stomach wall, detachable from the tubing under the effect of a simple pulling force, made of a non-biodegradable material selected solely for its elastomeric properties facilitating its installation by endoscopic tract and its evacuation by natural tracts,
b) by an end piece, positioned against the external face of the aforementioned flange, designed to maintain it against the stomach wall, made of a completely biodegradable copolymer or polymer whose bond with the tubing has a pulling breakage threshold that is a function of the formation time of the stoma.

The polymer or copolymer used is optimally selected among the structures PLA and PLA GA.

The functions, first, of installation and evacuation by natural tracts of the flange and, second, of its resistance during a set period of time, have been separated thus enabling selection of the flange for its own elastomeric properties and the end piece for its own biodegradability properties.

Such a design has an essential advantage of obtaining clinical results most appropriate to the functions sought, namely the disappearance of the risks of occlusion with mortal consequences and of anesthesia necessitated by the use of an endoscope.

We are thus, faced with a combination of means that is not taught in the cited prior art and does not follow from it in a manner obvious to a person of skill in the art.

The period of optimal healing of the stoma is approximately 21 days. Too short a period could lead to its poor healing with all the consequences that may arise mainly at the introduction of a replacement catheter.

The incidents resulting from this mainly relate to the incarceration of the flange between the walls, or the accidental passage of the administered nutritious products into the abdominal cavity. These incidents appear to be related to the removal by force of the gastrostomy tube through the stoma, leading to the disengagement of the flange and causing laceration of the stoma. The positioning of the replacement catheter in this case is uncertain.

PRESENTATION OF FIGURES

The characteristics and advantages of the invention will emerge more clearly upon reading the following detailed description of at least one preferred implementation thereof given by way of non-limiting example and illustrated in the attached drawing (single FIGURE) which sectionally represents a partial view of a catheter provided with a collar and a mouthpiece, sandwiching the stomach and abdominal walls.

DETAILED DESCRIPTION OF THE INVENTION

The illustrated percutaneous gastrostomy catheter is the type including:

a) a tubing (1) designed to pass through the stomach (4) and abdominal (5) walls of the subject;

b) an internal means of retention (2), joined to the aforementioned tubing (1), designed to be maintained pressed against the internal face of the stomach wall and to disengage itself from the aforementioned tubing by biodegradation;

c) an external flange (3), traversed by the tubing (1), designed to be pressed against the external face of the aforementioned abdominal wall (5) and exert, in cooperation with the internal means of retention (2), a pressure adapted to press the stomach wall (4) against the abdominal wall (5) in the area of the stoma.

The internal means of retention is constituted:

a) by a flange (21), positioned against the stomach wall (4), detachable from the tubing (1) under the effect of a simple pulling force, made of a non-biodegradable material selected solely for its elastomeric properties facilitating its installation via endoscopic tract and its evacuation via natural tracts;

b) by an end piece (22), positioned against the external face of the aforementioned flange (21), designed to maintain it against the stomach wall (4), made of a completely biodegradable copolymer or polymer whose bond with the tubing (1) has a pulling breakage threshold, by simple tension, that is a function of the formation time of the stoma.

The speed of biodegradation of the means of retention is programmed so that its mechanical characteristics are maintained at least until the adhesion of the stomach and abdominal wall between themselves.

The end piece (22), which is provided with an opening for the passage of the tubing (1), can be joined to the latter by gluing, welding, crimping or by any other known means.

The tubing (1) is generally made of a non-biodegradable biocompatible material such as, for example, silicone or polyurethane.

The choice of biodegradable copolymer or polymer suitable for the considered medical application was the subject of tests including synthesizing various polymers and copolymers into samples, immersed in a model of gastric fluid, with dimensions similar to those of the biodegradable internal means of retention concerned, capable of degrading within a well determined period (in particular between 1 and 3 months), having the physical and mechanical characteristics required, in terms of hardness or elasticity, shape changes, swelling due to the water, decomposition . . . .

Tests have been conducted on samples made with various polymers or copolymers of the types:

Polylactic acid such as PLA 50 ($Mn=21000$ g/mol) and PLA 50 ($Mn=46000$ g/mol);

Polylactic acid-glycolic acid such as PLA 37.5-GA 25 ($Mn=39000$ g/mol);

Triblocks PLA-PEG (poly ethylene glycol)-PLA such as PLA 50-PEG (20000)-PLA 50 ($Mn=277760$ g/mol), PLA 50-PEG (20000)-PLA 50 ($Mn=100600$ g/mol), PLA 50-PEG (6000)-PLA 50 ($Mn=56400$ g/mol), PLA 96-PEG 12000-PLA 96 ($Mn=68311$ g/mol), PLA 96-PEG 8000-PLA 96 ($Mn=71684$ g/mol) and PLA GA-PEG-PLA GA PLA.

The choice was made in the PLA class, and more optimally in the PLA GA class, of polymers, to implement the end pieces where the problems of shape memory and flexibility are not posed.

The end piece has a thickness optimally between 1 and 3 mm (non limiting) to also affect the rate of biodegradability.

Components having the effect of changing the mechanical characteristics and the rate of degradation as well as body tolerance can be added to the aforementioned copolymers.

Of course, the person of skill in the art will be able to implant the invention as described and depicted in applying and adapting known means.

It may also include other variations without departing from the scope of the invention which is determined by the terms of the claims.

The invention claimed is:

1. A percutaneous gastrostomy catheter, comprising:
   a) a tubing configured to pass through stomach and abdominal walls of a patient;
   b) an internal retainer, joined to the tubing, configured to be maintained pressed against an internal face of the stomach wall and to disengage itself from the tubing by biodegradation; and
   c) an external flange, traversed by the tubing, configured to be pressed against an external face of the abdominal wall and exert, in cooperation with the internal retainer, a pressure adapted to press an external face of the stomach wall against an internal face of the abdominal wall,
   characterized in that the internal retainer includes:
   an internal flange defining a first face and a second face opposed to the first face, the first face of the internal flange being configured to be pressed against an internal face of the stomach wall, the internal flange being detachable from the tubing under the effect of a simple pulling force, the internal flange being made of a non-biodegradable material having elastomeric properties facilitating installation of the internal flange by endoscopic tract and evacuation of the internal flange by natural tracts; and
   an end piece pressed against the second face of the internal flange, such that the internal flange is between the end piece and the external flange, the end piece being configured to maintain the internal flange against the stomach wall, the end piece being made of a completely biodegradable copolymer or polymer having a bond with the tubing.

2. A catheter, according to claim 1, characterized in that the polymer used is of the PLA type.

3. A catheter, according to claim 1, characterized in that the copolymer used is of the PLA GA type.

4. A catheter, according to claim 1, characterized in that the end piece used has a thickness between 1 and 3 mm.

5. A catheter, according to claim 1, characterized in that the end piece has a degradation time in the range of 1 to 3 months.

* * * * *